(12) United States Patent
Crunkilton et al.

(10) Patent No.: US 8,334,637 B2
(45) Date of Patent: Dec. 18, 2012

(54) TRANSDUCER WITH SHIELD

(75) Inventors: Jeffrey R. Crunkilton, Everett, WA (US); Charles S. Desilets, Edmonds, WA (US); Greg P. Darlington, Snohomish, WA (US); Jens U. Quistgaard, Seattle, WA (US)

(73) Assignee: LipoSonix, Inc., Hayward, CA (US)

( * ) Notice: Subject to any disclaimer, the term of this patent is extended or adjusted under 35 U.S.C. 154(b) by 301 days.

(21) Appl. No.: 12/636,538

(22) Filed: Dec. 11, 2009

(65) Prior Publication Data

US 2011/0140573 A1 Jun. 16, 2011

Related U.S. Application Data

(62) Division of application No. 11/532,745, filed on Sep. 18, 2006, now Pat. No. 7,652,411.

(51) Int. Cl.
*H01L 41/08* (2006.01)
(52) U.S. Cl. ...................................... 310/334
(58) Field of Classification Search .......... 310/334–337, 310/800, 358, 369, 371
See application file for complete search history.

(56) References Cited

U.S. PATENT DOCUMENTS

| | | | |
|---|---|---|---|
| 2,487,962 A * | 11/1949 | Arndt, Jr. ...................... 310/328 |
| 2,565,159 A * | 8/1951 | Williams ...................... 310/335 |
| 3,331,970 A | 7/1967 | Dundon |
| 3,518,460 A | 6/1970 | Wood et al. |
| 3,849,679 A * | 11/1974 | Massa |
| 4,025,805 A * | 5/1977 | Coltman et al. .............. 310/335 |
| 4,190,783 A | 2/1980 | Massa |
| 4,190,784 A | 2/1980 | Massa |
| 4,260,928 A | 4/1981 | Salem |
| 4,316,115 A | 2/1982 | Wilson et al. |
| 4,440,983 A | 4/1984 | Facoetti et al. |
| 4,600,851 A | 7/1986 | Isayama et al. |
| 6,500,133 B2 * | 12/2002 | Martin et al. ..................... 601/3 |
| 6,747,395 B1 | 6/2004 | Satoh et al. |
| 7,898,159 B2 * | 3/2011 | Heydt et al. ................... 310/317 |
| 2004/0116803 A1 | 6/2004 | Jascob et al. |

FOREIGN PATENT DOCUMENTS

JP 07178109 A 7/1995

OTHER PUBLICATIONS

International Search Report and Written Opinion of PCT Application No. PCT/US07/75634, dated Sep. 4, 2008, 10 pages total.
Official Action and translation dated Jun. 7, 2012 issued in related japanese Patent Application No. 2009-528371.

* cited by examiner

*Primary Examiner* — Mark Budd
(74) *Attorney, Agent, or Firm* — Wood, Herron & Evans, LLP

(57) ABSTRACT

A physical shield placed on the face of a high intensity focused ultrasound transducer for medical applications is described. The shield may be shaped or angled to match a particular pattern of mechanical or acoustic energy that may damage the transducer during operation. The shield may be ablative, replaceable or modified as needed. Methods of manufacturing a transducer with a shield are also disclosed.

21 Claims, 13 Drawing Sheets

TRANSDUCER WITH SHIELD

CROSS-REFERENCE TO RELATED APPLICATIONS

This application is a continuation of U.S. application Ser. No.: 11/532,745, filed on Sep. 18, 2006, the full disclosure of which is incorporated herein by reference.

BACKGROUND OF THE INVENTION

1. Field of the Invention

The present invention relates to a high intensity focused ultrasound transducer for medical applications, the transducer generally having a shield physically attached to the transducer face.

2. Description of the Background Art

High intensity focused ultrasound (HIFU) transducers are finding increased usage in medical procedures. Similar to their cousins in diagnostic imaging, HIFU transducers share many of the same structural components. In HIFU transducers, the piezoelectric material is selected and crafted to produce the desired frequency, intensity, and total power to produce HIFU levels sufficient to lyse targeted tissue. Once a piezoelectric material has been selected and shaped, the piezoelectric material is coated with an electrically conductive material (a metallization layer) on both the front and back faces of the transducer. The piezoelectric material is 'poled' by applying a strong electric potential between the electrodes, activating the piezoelectric material. An electrode is connected to each metalized surface, and connected to an electrical power generator. A periodically varying potential difference is applied between the electrodes causing the piezoelectric material to vibrate longitudinally at the alternation frequency. The back transducer face generally interfaces with air or a low acoustic impedance absorber-backing; a front transducer face interfaces with the acoustic load, sometimes through an intermediate impedance matching material layer. This configuration causes an ultrasound wave front to be propagated longitudinally through the front face. Although the transducer face may be flat or shaped, in HIFU applications the front face is generally "bowl" shaped to provide spherical focusing.

In medical high intensity focused ultrasound (HIFU) applications, transducers are generally coupled to a patient using fluids. The frequency, intensity, and power used in HIFU therapy is such that reflections from the patient interface are sufficient to induce cavitation and micro-streaming of coupling agent particles (including water molecules) that can cause damage to the face of the transducer. Damage to the face of the transducer produces a number of undesirable side effects, including delamination of the matching layer from the piezoelectric ceramic, erosion of metallization on the piezoelectric material, loss of proper focus of ultrasound energy (which leads to attenuation and thermal build-up in areas that may pose a health risk to a patient), and physical destruction of the piezoelectric material used to make the transducer.

Various attempts to solve this problem have thus far proved to be unsatisfactory. In some HIFU applications, transducer shielding is sometimes found in the form of an acoustic lens placed across the transducer face. The acoustic lens provides the dual functionality of providing a degree of focusing of the ultrasound energy while simultaneously protecting the piezoelectric material from damage. Damage may come from accidental contact of the transducer face with foreign objects, or from mechanical effects of HIFU reflections in the medium used to couple the transducer to a target surface. The use of an acoustic lens has several disadvantages.

One disadvantage of this solution is that the lens also acts as a boundary layer between the transducer "stack" (piezoelectric material plus any matching layers and backing) and the target tissue. Ultrasound energy is lost through attenuation in the lens. Reflection and refraction of ultrasound energy are also problems which must be dealt with. As power and intensity increase in a HIFU transducer, the associated difficulties accompanying the use of a lens can become too great to overcome.

Thus there remains a need for a HIFU transducer that can withstand the disturbances created when the transducer is activated.

There is further a need for a HIFU transducer to be operable at extremely high operating intensities and total power levels.

There is still another need for extending the useful life of a transducer that has been damaged by disturbances.

BRIEF SUMMARY OF THE INVENTION

An objective of the present invention is to provide a HIFU transducer resistant to mechanical damage associated with HIFU usage.

Another objective is to provide a shield that can protect the face of the transducer without substantial degradation of the transducer's performance.

Still another objective is to provide a shield that does not interfere with ultrasound energy transmission from the transducer.

Yet another objective is to provide a transducer shield that is replaceable if needed.

These and other objectives are met by using a high intensity focused ultrasound transducer with a shield. In one embodiment the HIFU transducer with a shield has a front face, a back face, and a shield attached to the front face.

In another embodiment, there is a high intensity focused ultrasound transducer having a flat or substantially bowl shaped front side, and a shield attached to the front side. The transducer face desirably has a region on the front face that is not electrically driven (non-driven region, wholly or partially piezoelectric inert region), either due to electrical isolation or material formation, so that the non-driven region is not an ultrasound emitting surface. The non-driven region is covered with a material that acts as a shield against damage to the transducer when the active region of the transducer is activated and reflected energy impinges on the transducer face.

In another embodiment the transducer has an aperture there through the front face of the transducer and aligned substantially normal to the front face of the transducer. The aperture extends from the front face to the back side of the transducer. Optionally the aperture may be filled.

DETAILED DESCRIPTION OF THE INVENTION

Figure 1A:
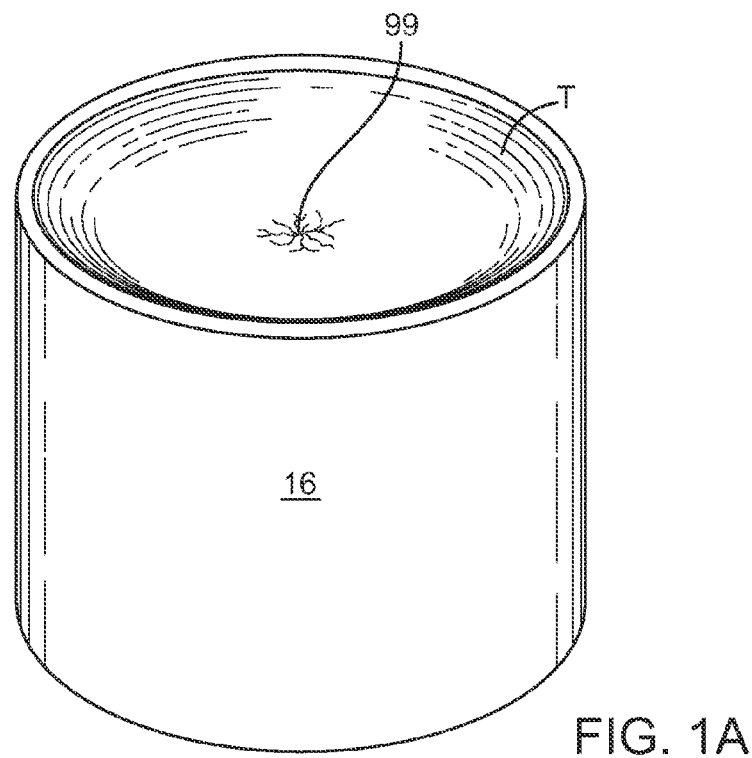
FIGS. 1A-1B illustrate a damaged HIFU transducer.

Described herein are various transducers designed to resist destructive reflected energy encountered when the transducers are excited. In particular, the invention relates to high intensity focused ultrasound transducers used in medical applications. These transducers see frequent use on human patients and as such insuring high and consistent quality of transducer performance is highly desirable.

In one embodiment, there is a HIFU transducer having a shield placed on the front face of the transducer.

In an alternative embodiment, there is a HIFU transducer having an electrically isolated region on the front face of the transducer, and a shield incorporated within the electrically isolated region.

In another embodiment, there is a HIFU transducer having an aperture there through, and a reinforced back plate having a low acoustic impedance layer to serve as a proper back plane to provide for primarily forward ultrasound propagation.

In another embodiment, there is a HIFU transducer having an aperture through the piezoelectric material, and a non piezoelectric plug filling the aperture.

In each of the embodiments there are various configurations of the transducer material, the metallization layers, and any matching layers, that provide for proper operation of the transducer having a shield. The main component is the transducer itself. This may be a specially made transducer as described herein, or an existing transducer modified by the methods and procedures described herein, to make a transducer with a shield.

The region of the transducer under the shield may be designed in a variety of alternative embodiments. In one embodiment, the region under the shield is the same as the rest of the transducer, and the shield is optimized to minimize the stress of ultrasound passing through it so the shield offers protection against physical degradation of the front face of the transducer, while not damaging the transducer by sitting on an active region of the transducer face.

Alternatively the region under the shield may produce a lower acoustic pressure than the unshielded portions of the transducer when it is excited. Desirably, the piezoelectric material under the shield now produces less acoustic pressure than those areas which are unshielded. The level of reduction may be any amount of acoustic pressure less than the normal unshielded transducer output. Ultrasound energy may still be emitted through this region from fringing piezoelectric elements that radiate through the shielded volume, and from reverberations in the transducer under the shield. This nondriven region is not directly driven, but may produce ultrasound energy due to being indirectly driven (through fringing electrical effects) or produce ultrasound through fringing mechanical effects or reverberation effects from those regions which are actively driven. This non-driven region may be produced in a variety of ways. For example the transducer may have a non-piezoelectric material in the region of the shield. This can be done by breaking the metallization before poling to produce an unpoled, and therefore substantially inactive, portion of piezoelectric material, or by replacing the region of piezoelectric material with a non piezoelectric material. Small amounts of ultrasound energy can be emitted from non-driven sections of the transducer through acoustic or electrical cross-coupling mechanisms. Alternatively the transducer may have a uniform material and manufacturing form, and rely on electrical isolation to prohibit the piezoelectric effect in the desired region. This can be achieved by isolating the desired region from the electrodes used to create the circuit around the transducer. In one embodiment the shield region can be isolated by scribing through the metallization layer so the electrical continuity of the front and back surface of the transducer are interrupted. Thus when the back face of the transducer is electrically stimulated, a region on the back face will not be electrically stimulated directly except through cross-coupling mechanisms. The region on the front plane that is electrically isolated desirably conforms to the same area that is electrically isolated on the back layer. In an alternative embodiment, electrical isolation may be achieved by removing the metallization layer and/or matching layers from the region to be electrically isolated. The removal may take the form of either not laying down the metallization layer on the transducer in the regions to be electrically isolated, or by removing the metallization layers after they are deposited on the transducer. Removal of the metallization layer may come from sand blasting, grinding, chemical etching, laser etching, or any other means of reliably removing metal from the transducer face in a depth controlled operation.

In a third embodiment, the region under the shield may be completely removed and replaced with an inert material to provide complete isolation of any ultrasonic fringe energy produced by the rest of the transducer.

Once the region is electrically isolated, the shield is attached to the transducer front face. Desirably the shield is a polymer material having a balance of resilience and absorptive qualities to protect the transducer against mechanical damage. Thus the polymer material is desirably able to absorb mechanical energy that may impact the transducer face during transducer operation. The polymer may dampen the mechanical energy to reduce or eliminate mechanical impact on the transducer face, or the polymer may act as an ablative shield. In the latter case, mechanical energy such as cavitation or micro-streaming, would damage the polymer shield without damaging the transducer itself. The shield may be made of any nonconductive material being relatively impervious to mechanical effects caused by cavitation and micro-streaming.

Alternatively the shield may be an ablative shield so any mechanical damage that might otherwise damage the transducer is done to the shield instead. A polymer shield is desirable in it offers the combined features of both absorption (dampening) and ablative properties. Polymer shields are readily formed and attached to transducers as well. Non-polymer materials may also operate as an ablative shield. In the case of an ablative shield, it is desirable to provide either circulation of the coupling fluid or direct removal of the ablative particles of the shield, so these particles do not themselves become nuclei for cavitation.

The size, shape and material of the shield will vary depending on the performance characteristics of the transducer. In one embodiment, there is a transducer operating at 2 MHz capable of producing 400 W of total acoustic energy. The transducer is 38 mm in diameter and incorporates a non-driven 7 mm diameter center section. The shield on the face of the transducer is centrally positioned over the non-driven region and is formed of a soft rubber or plastic having a SHORE A value between 20-60. One potential material for the shield may be polyurethane, or a like compound.

In another embodiment the shield does not function in an ablative way but is formed of a harder material having a SHORE D value of 10 to 80. This layer may be flat or of a special shape to reflect and scatter the incoming acoustic energy or micro-streaming material flow. This could be an additional operation or incorporated into the matching layer during casting.

In another embodiment the shield could consist of a thin, highly reflective metal foil. This layer could be applied to re-reflect the incoming acoustic energy or micro-streaming. This could be an additional operation or incorporated into the matching layer during casting.

A generic mold template may be used to create the transducer with a shield. The mold has a base having an outside face, an inside face and a foot print sufficient to cover the face of the transducer. A guide ring is connected to the base. The guide ring is designed to receive the transducer. A riser extends from the inside face of the base. The riser has a base end in contact with the base, and a contact end, designed to touch the face of the transducer when the mold is properly mated with the transducer. The mold may be any shape or size, so long as the guide ring can properly guide the mold into place. One can imagine the base and guide ring behaving analogous to an end cap for the transducer. The riser extends from the inside face of the base, to the transducer face, when the mold is properly fitted over the transducer. Thus the riser, guide ring and base may desirably be fabricated to mate specifically with the configuration of a particular transducer. The riser desirably makes contact with the transducer over an area coinciding with the non-driven region of the transducer. As described below, one manner of defining the size of the non-driven region is by determining the contact surface area the riser makes with the front face of the transducer.

The mold may be modified in numerous ways to create additional molds useful in making a transducer with a shield. In one embodiment, the mold may have a serrated lip on the riser facing the transducer face. In another embodiment the mold may have a small indent or cavity at the top of the riser where the riser comes into contact with the face of the transducer. In another embodiment, there is an aperture extending through the base and the riser, so that a region of the transducer face is accessible through the mold. The mold may also have a small hole through the base (not coinciding with the riser) so that air may pass in and out of the inside volume of the mold.

Referring now to the drawings, it should be understood the drawing figures are provided to enhance the description provided. Elements shown in the figures are not necessarily illustrated to scale with respect to other drawings, or other parts within the same drawing. Nor should the parts or figures be taken in any absolute sense of actual design elements other than as illustrations of embodiments for the purpose of understanding the disclosure herein.

Figure 1B:
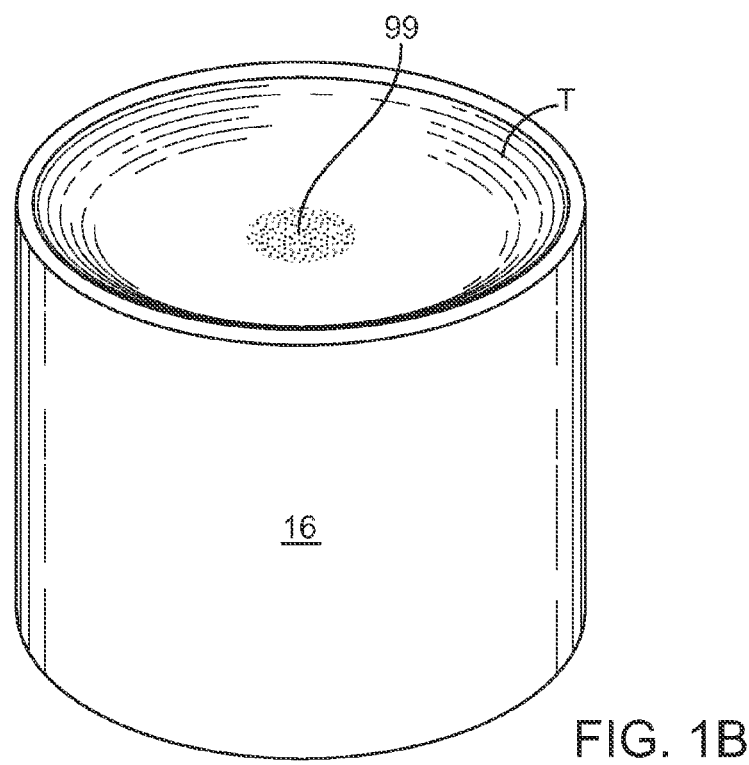
Figure 2A:
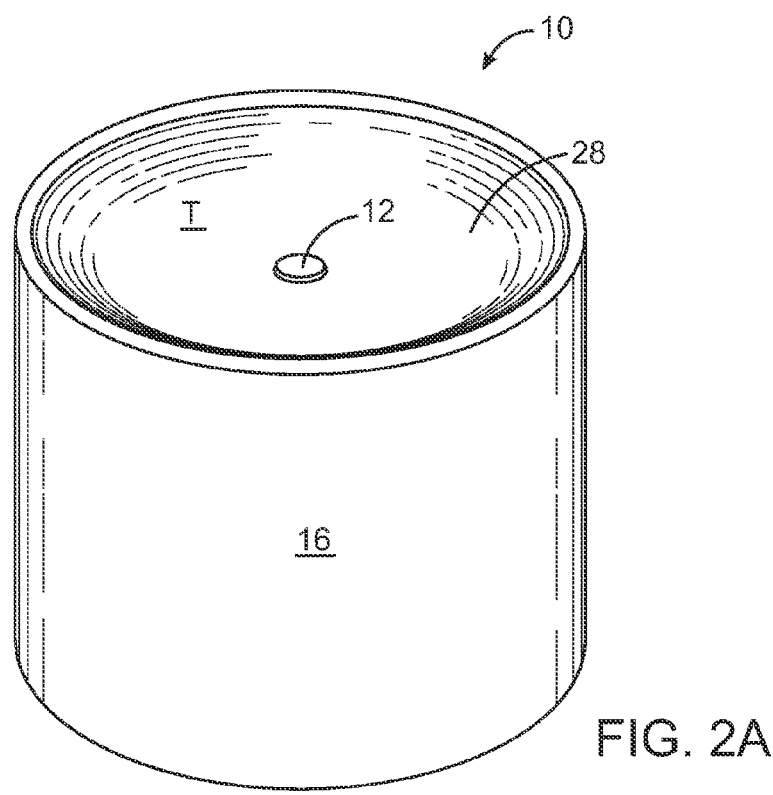
FIGS. 2A-2O illustrates a HIFU transducer with a shield and various cross sections.
Figure 2B:
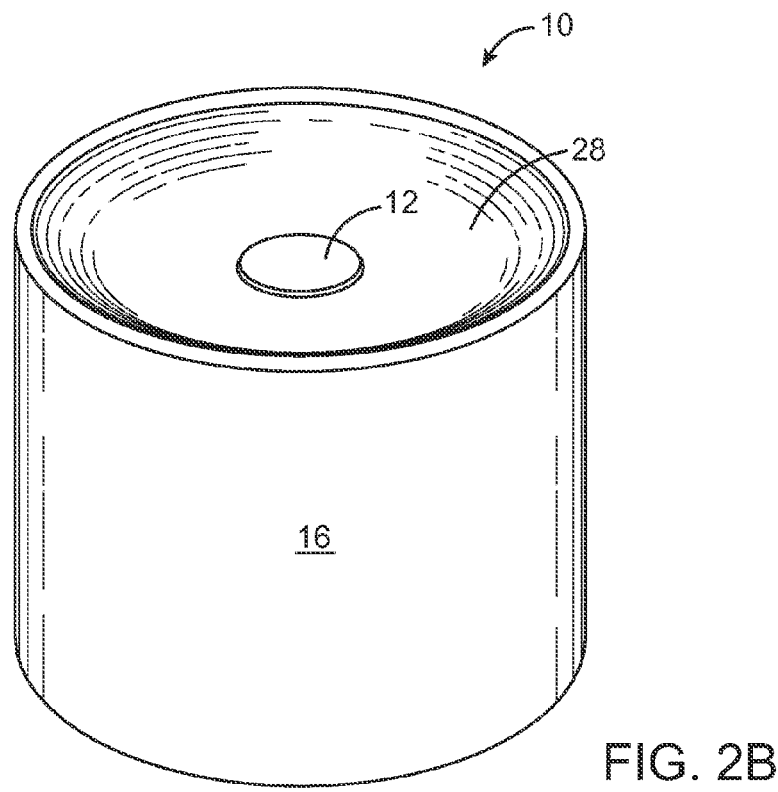

Turning now to the drawings, areas of physical damage 99 may appear on HIFU transducers as shown in FIGS. 1A and 1B. HIFU treatment may cause unintended and undesirable physical and thermal effects near the transducer surface which may produce cracks in the transducer front face (FIG. 1A), or may pit or cause imperfections in the transducer face to occur (FIG. 1B) Damage to the transducer face is undesirable and may adversely effect the operation of the transducer. The physical damage to the transducer may be minimized by providing a shield on the transducer front face. A transducer with a shield 10 is shown in FIGS. 2A-2B. The transducer T is mounted in a transducer housing 16. The shield 12 is positioned in the middle of the transducer T. The size and shape of the shield are desirably made to match the pattern of damage the transducer would experience without a shield. While the damage patterns shown in FIGS. 1A-1B are centered in the transducer, different medical applications will produce damage in different areas of the front face. The shield need not be placed in the center, but can be placed on any area of the transducer front face desired. One need only identify the region where damage is likely to occur and provide a transducer with a shield as appropriate. Determining damage locations (and therefore optimum shield locations) can be done through experimentation or computer modeling. Cross section views of the transducer with shield are shown in FIGS. 2C-2G, and FIGS. 2I-2O.

Figure 2C:
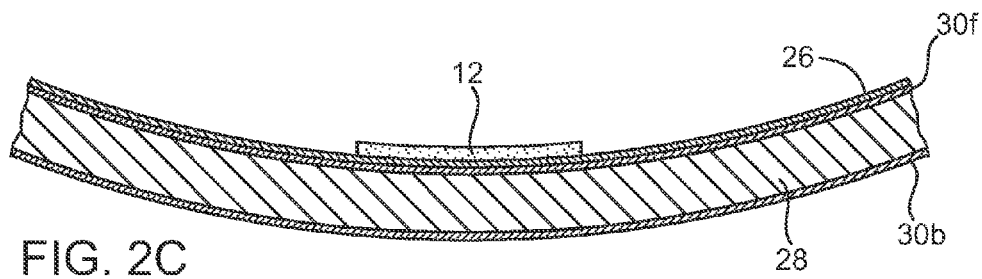

FIG. 2C illustrates one embodiment having a shield 12 placed directly on top of the face of the transducer T with no modification to the matching layers of the piezoelectric layer.

Figure 2D:
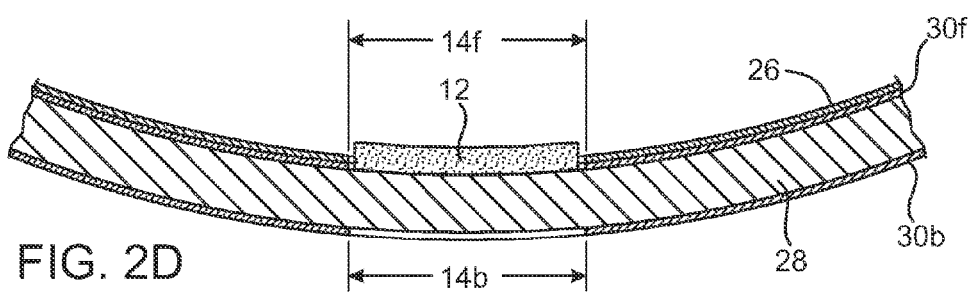

In FIG. 2D there is shown a cross section where the front metallization layer 30f has been removed, along with any matching layer 26 that may be used on the front face of the transducer. The shield 12 is attached directly to the piezoelectric material layer 28. To prevent the piezoelectric material under the shield from generating ultrasound energy when the transducer is excited, two regions are electrically insulated (or isolated) from the transducer circuit. These correspond to a front electrically isolated region 14f, and a back electrically isolated region 14b. Electrical isolation may be achieved by either scribing a pair of corresponding gaps in the metallization layers 30f, 30b (FIG. 2E), or by removing the metallization layers in the electrically isolated regions, such as the front face in FIG. 2D. The scribed gaps may be circular or any desired shape. Scribing may be done by any means capable of creating a gap space in the metallization layer wide enough to electrically isolate the desired region. The gap space may be physically scribed using a mechanical device (like a cookie cutter mold), chemically removed, laser etched or any other means of removing the metallization. The gap may also be created by laying down a mask on the transducer surface prior to metallization of the transducer surfaces. Once isolation of the metallization layer is completed, the mask is removed (see below), creating the desired gap space.

Figure 2E:
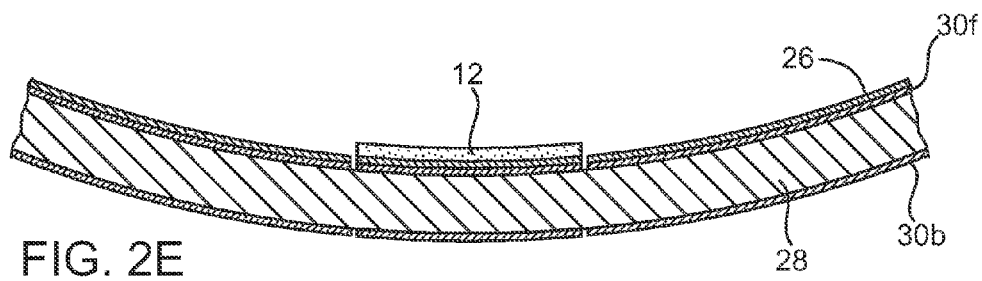
Figure 2F:
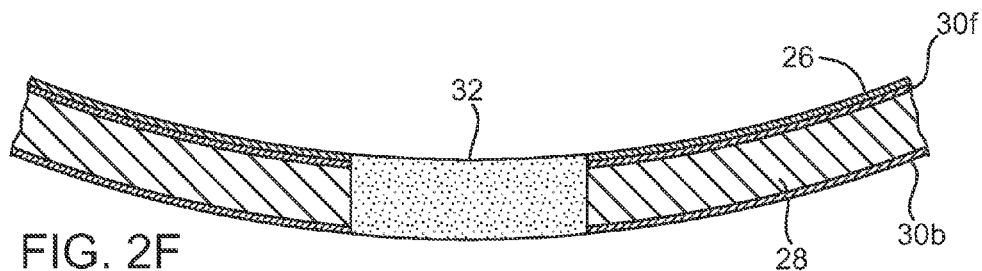

The non-driven region of the transducer may be formed by replacing the piezoelectric material in the transducer with a plug, or forming the transducer in a manner that the piezoelectric material is neutralized and forms a non-driven region. Examples are shown now in FIGS. 2F and 2G. In FIG. 2F a non-driven region 32 is created by either replacing the piezoelectric material with an inert matter that does not produce substantial ultrasonic vibrations, or is piezoelectric material that is neutralized by breaking the metallization before poling to produce an unpoled, and therefore substantially inactive, portion of piezoelectric material. Alternatively the central piezoelectric material may be isolated using an insulating donut or washer 34.

Figure 2G:
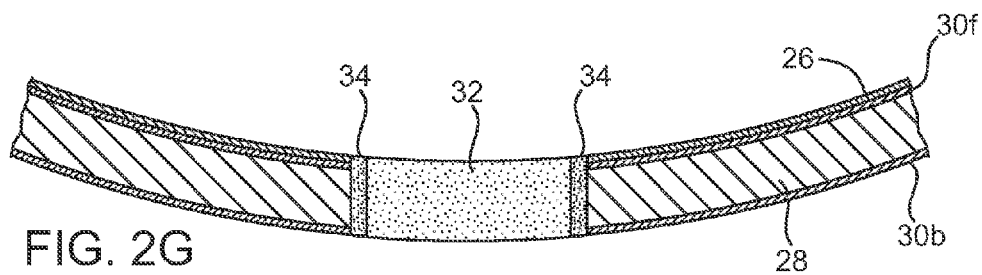
Figure 2H:
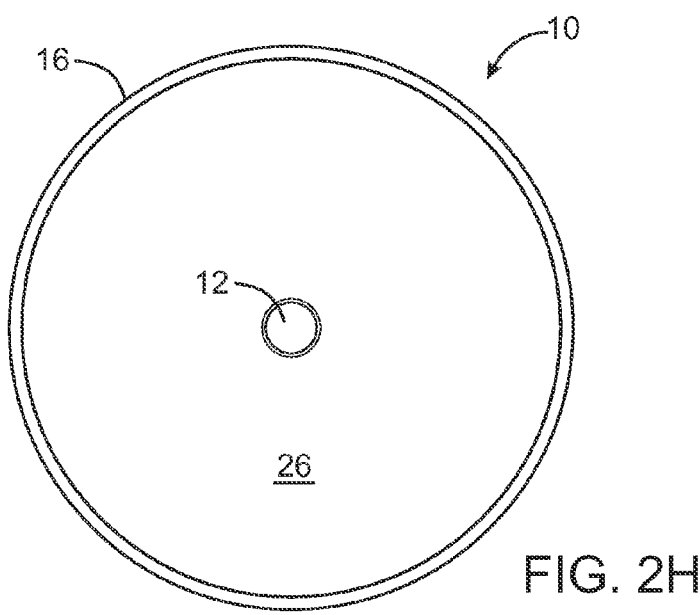
Figure 2I:
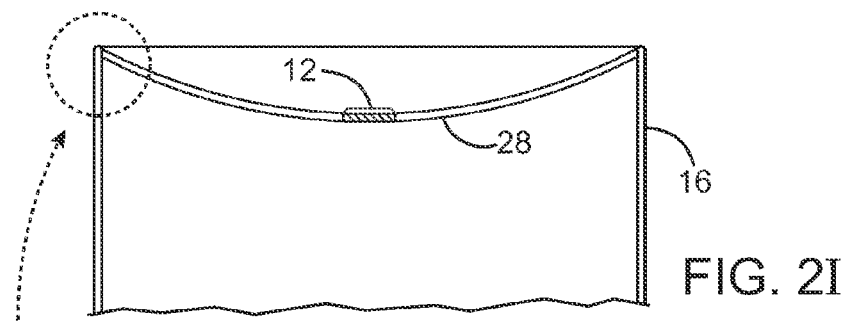
Figure 2J:
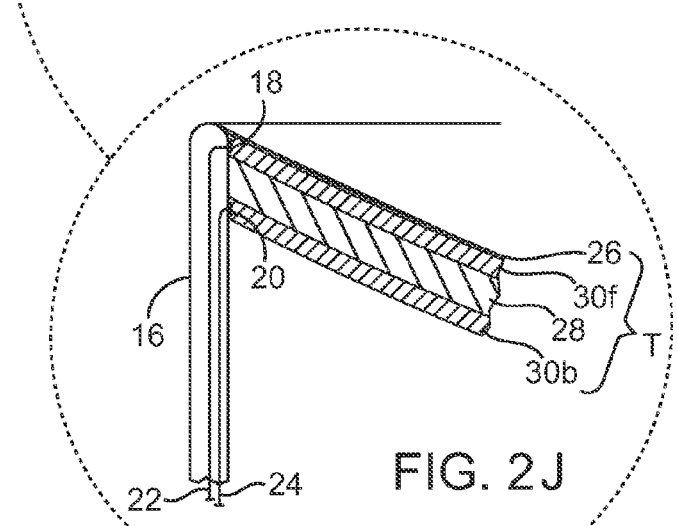
Figure 2K:
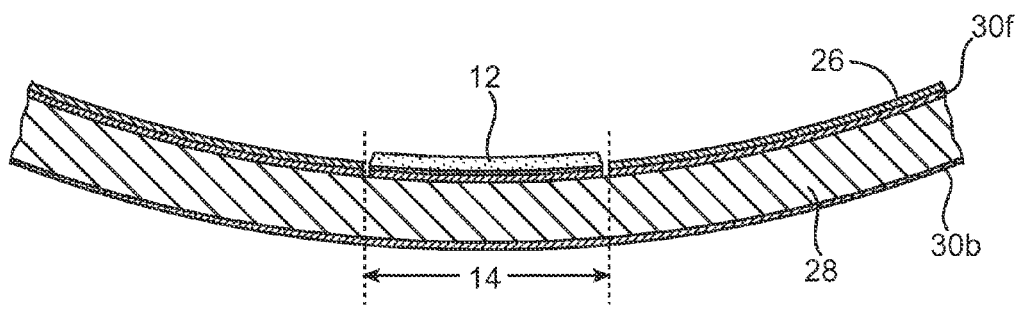
Figure 2L:
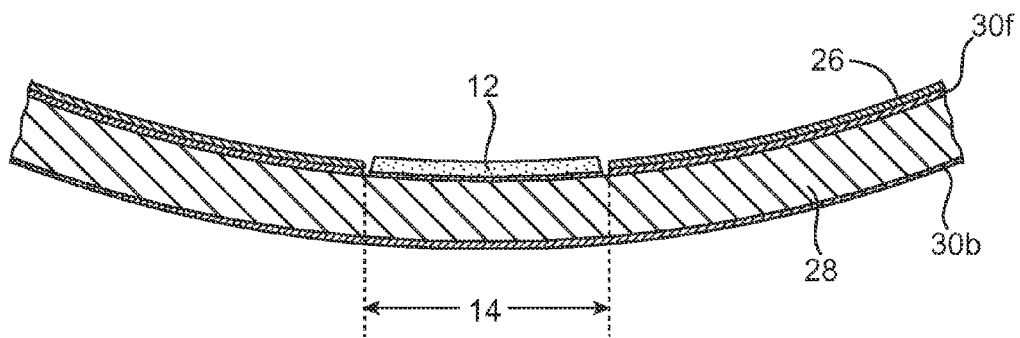
Figure 2M:
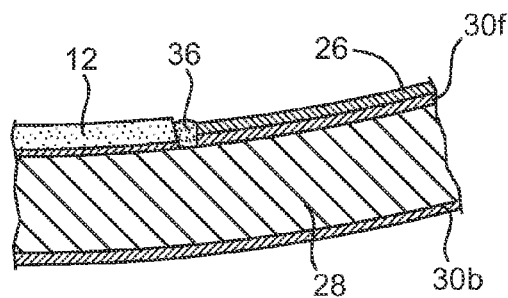
Figure 2N:
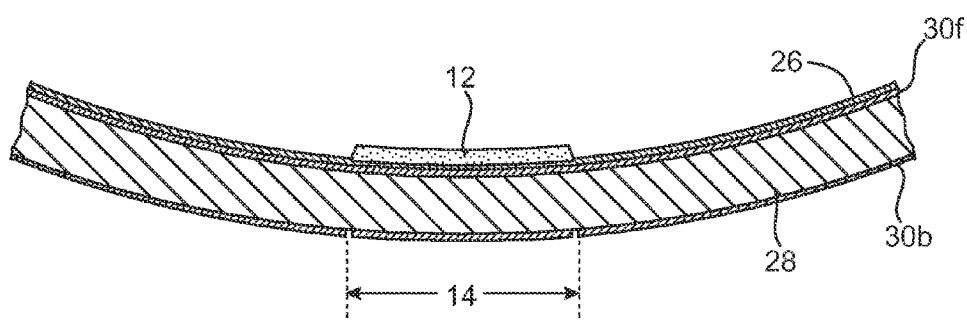
Figure 2O:
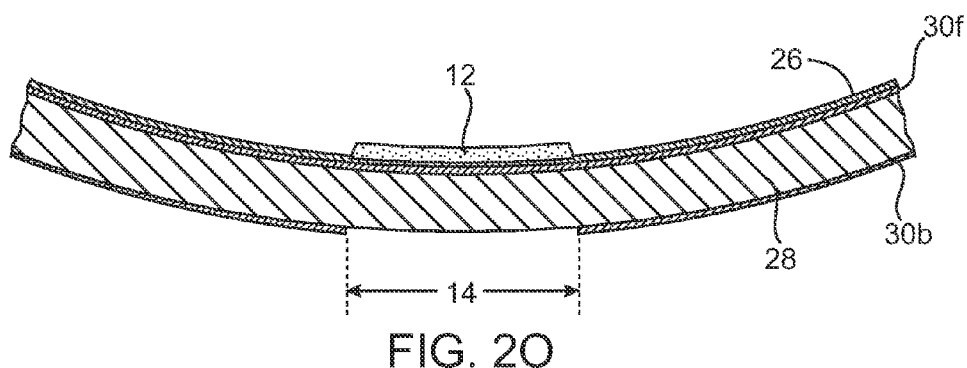

Various forms of a piezoelectric non-driven region are shown in FIGS. 2K-2O. The illustrations provide for having the front side metallization isolated for shield placement (FIGS. 2K-2M) or having the back side isolated (FIGS. 2N-2O). In all these figures the isolation is shown as being a cross section of a ring extending from the exterior of the layers, and going down to the piezoelectric layer 28. Again the ring is merely illustrative and it should be appreciated that the metallization layers and matching layer may be completely removed in the non-driven region while providing the same effectiveness. To prevent de-lamination or contamination on any exposed layers of the transducer, the etched ring or other aperture in the metallization or matching layers may be filled with a material 36 to protect the structural integrity of the transducer. While desirable, it is not necessary to remove the metallization layer on both the front and back of the transducer to create a region of reduced piezoelectric activity 14.

Creation of an electronically isolated region in not required in order for the transducer with a shield to operate properly. In one alternative embodiment, the piezoelectric layer of the transducer is non-operable in the region where the shield is to be placed. An inactive region of the piezoelectric layer may be built into the design of the transducer, or removed from the transducer after manufacturing (FIGS. 2F-2G). In piezoelectric inactivity is part of the transducer during construction, it can be achieved by cutting or isolating a region of the metallization layer. This would cause an insulating gap in the metallization layer rendering the isolated portion electrically inactive. This electrically isolated area would not produce the desired polarizing effect within the piezoelectric material between the isolated plane. Alternatively the volume of the transducer to be rendered non-driven may be done by physically removing it from the transducer.

Physical removal can be done through numerous means. For example, if the transducer is placed into a sandwich mold having matching apertures on each side, the area desired to be removed may be drilled out. The aperture is desirably filled with a material or compound that will preserve the structural integrity of the transducer while not adversely effecting transducer performance. Furthermore the material desirably provides some shielding benefit. Any suitable material may be used. In addition to polymers and non oxidizing metal alloys previously described, conducting metals may also be suitable, since a conducting metal does not adversely affect performance since there is no piezoelectric activity in the non-driven region. Care needs to be taken if a conducting metal is used, so as to preserve the circuit used to make the transducer operate. The filler material may need a non-conductive insulation, such as a rubber or plastic ring.

Thus there are numerous ways to create the non-driven region 14 on the transducer prior to the application of the shield 12. The shield 12 may be laid down on the physical piezoelectric layer 28 or on one of the metallization layers 30f, 26 on the front face of the transducer T (FIG. 2E). If the transducer T has an aperture with a filler incorporated into it, the filler material serves as a shield (FIG. 2F).

In another embodiment the transducer can be made with an aperture, and the aperture can be preserved. In this embodiment the back of the transducer requires a special back plate that incorporates a metallization layer, as well as an acoustic impedance matching layer, so as to preserve the effective "forward" facing transmission characteristics of the transducer. Desirably the transducer also has a modified housing to provide the needed structural support for the transducer when it is active. The shielding for the transducer in this embodiment may be a plate or cup lined up with the aperture through the transducer to protect the transducer from behind. Since micro-streaming or cavitation can pose a risk of physical damage to the transducer, a shield is still needed to protect the transducer even if the micro-streaming or cavitation pattern extends behind the plane of the transducer.

The completed transducer is shown in plan view in FIG. 2G, and profile cross section in FIG. 2I. The transducer with shield 10 has a housing 16 for structural support. The housing may be any shape or form conducive for the desired use of the transducer 26. A shield element 12 is placed on the transducer surface to protect the transducer against physical damage. The transducer T is shown in magnification in FIG. 2J. The piezoelectric layer 28 is shown having a front metallization layer 30f and a back metallization layer 30b. There is also shown a matching layer 26 on the front surface of the transducer. A pair of electrodes 18, 20 are connected to the front and back metallization layers to provide the electrical circuit needed to create ultrasound. The electrodes 18, 20 are connected to lead wires 22, 24 which extend to an electrical power generator (not shown). The piezoelectric layer 28, metallization layers 30f, 30b and optional matching layer 26 are collectively referred to as the transducer T. A HIFU transducer may be modified into a transducer with a shield by modifying the front and back face of the transducer appropriately.

Figure 3A:
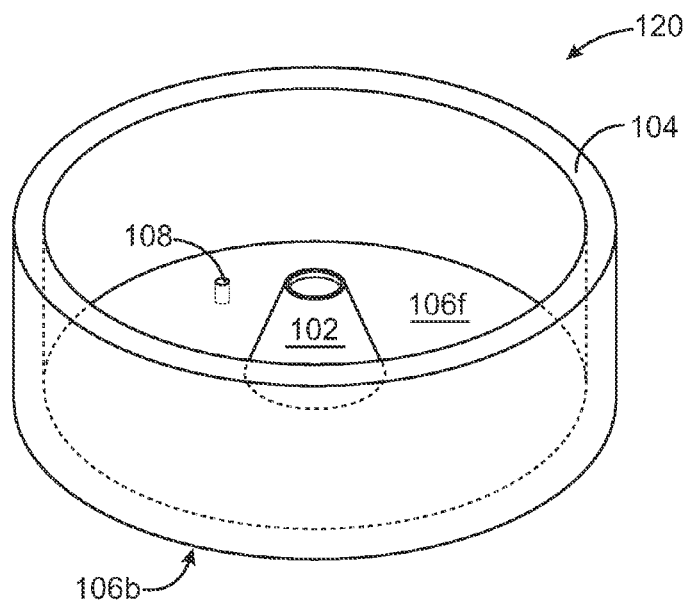
FIGS. 3A-3B and 4A-4G show various molds for making a HIFU transducer with a shield.
Figure 3B:
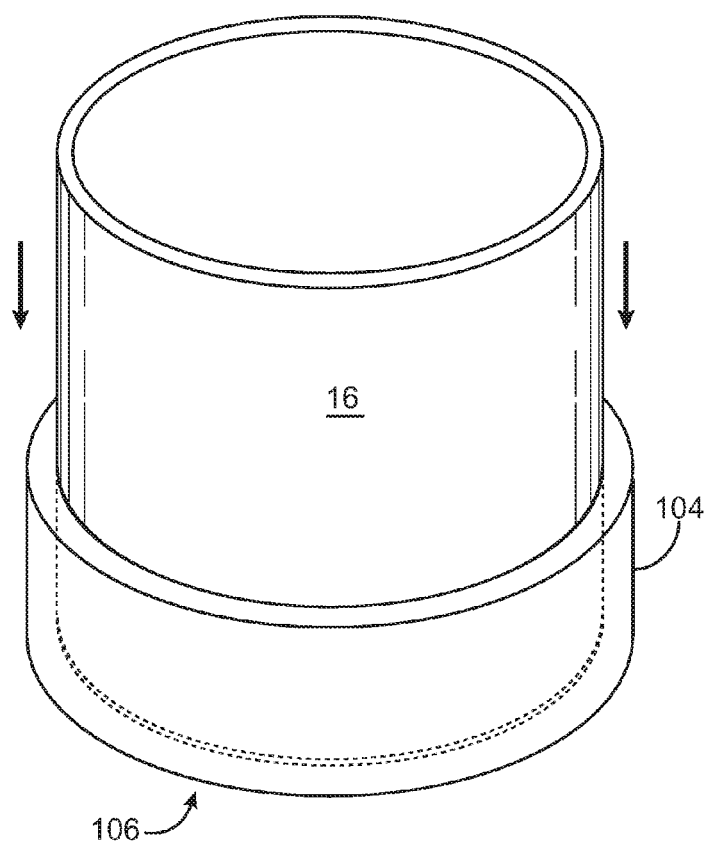
Figure 4A:
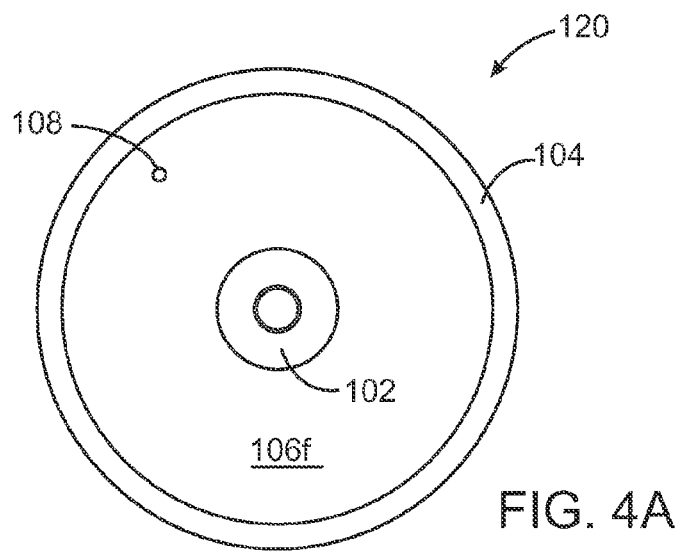

A mold is provided for the modification of a transducer. The basic form of the mold 120 is shown in FIG. 3A. The mold has a base 106 with a front side 106f and a back side 106b. A guide ring 104 is connected to the base 106 to receive a transducer T or transducer housing 16 (FIG. 3B). A riser 102 is shown attached to the base front side 106f. The riser 102 has one end attached to the base 106, and the other end designed to make contact with the front face of the transducer. In a front plan view, as provided in FIG. 4A, the riser 102 may contain a dimple or depression 114. The depression 114 may be formed in the riser 102, or may be the result of the top end of the riser having a lip 110.

Figure 4B:
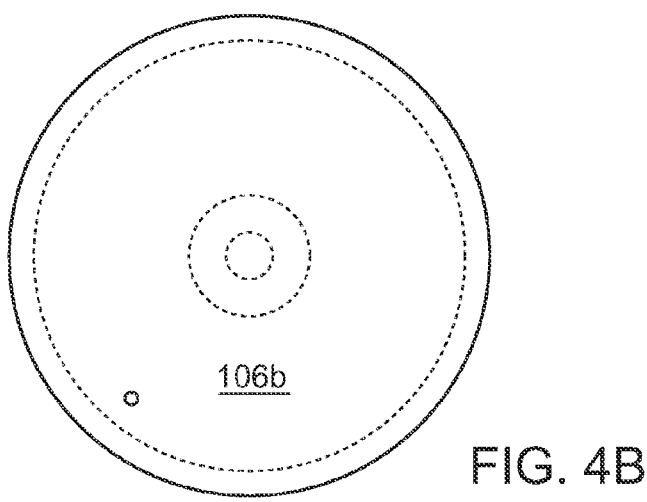

The mold 120 is now shown in greater detail in FIGS. 4A-4G. A top view is provided in FIG. 4A. The riser 102 is shown centrally positioned, though once again it is important to remember the position of the riser may be adjusted to adapt to any portion of the front face of the transducer. The mold front 106f faces the transducer face when the mold is pressed against the transducer or transducer housing, and the guide ring 104 is adapted to receive the transducer housing 16. An optional air hole 108 is also provided. The air hole 108 can be used to allow for gas exchange between the transducer and the outside environment when the transducer and mold are pressed together. FIG. 4B shows the back side of the mold with the front features presented in dotted lines.

Various forms of the riser 102 are now presented. In one embodiment there is a riser having a serrated lip (FIG. 4D) used for creating a circular shaped scribe in the matching or metallization layer on the face of the transducer. The mold 120 would be pressed against the transducer face and the riser 102 would extend sufficiently from the front face of the mold to make contact with the transducer. The mold and transducer may then be rotated relative to each other so the serrated edge of the riser lip 112 inscribes a ring in the transducer and creates an electrically isolated region.

Figure 4C:
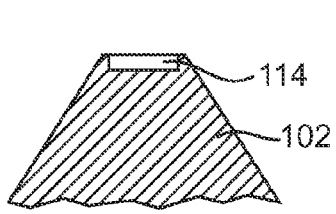
Figure 4D:
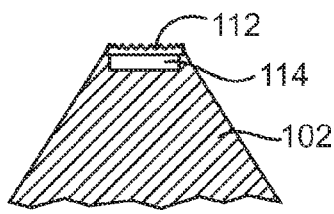
Figure 4E:
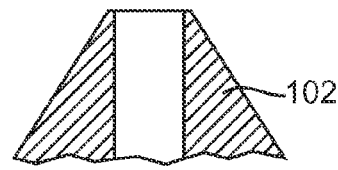

Alternatively, the riser 102 may have an aperture there through, which extends from the tip of the riser and extends through the base of the mold so that a bore hole is created allowing access to an isolated region of the transducer face from outside the mold (FIG. 4E). In this embodiment the isolated region can be created by etching or sand blasting the exposed portion of the transducer face through the aperture in the riser.

Once the electrically isolated region is created, a riser having sufficient height to touch the transducer face is now used with the mold to assist in the placement of the shield (FIG. 4C). In one embodiment, a precise amount of liquid polymer can be placed into the beveled region 114 of the riser. The mold 120 is then placed against the front face of the transducer and the entire assembly is inverted so gravity pulls the liquid polymer on to the transducer front face. The beveled region 114 defines the size and depth of the shield, and helps keep the polymer in place while it dries.

Figure 4F:
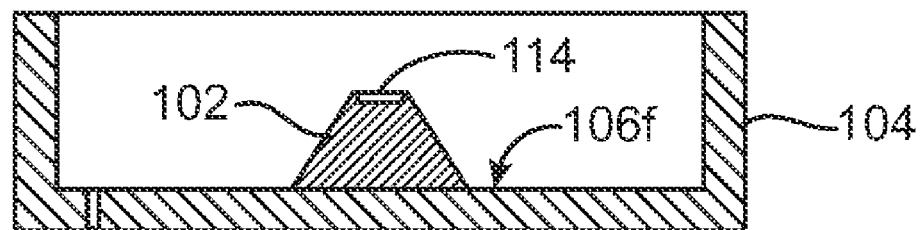
Figure 4G:
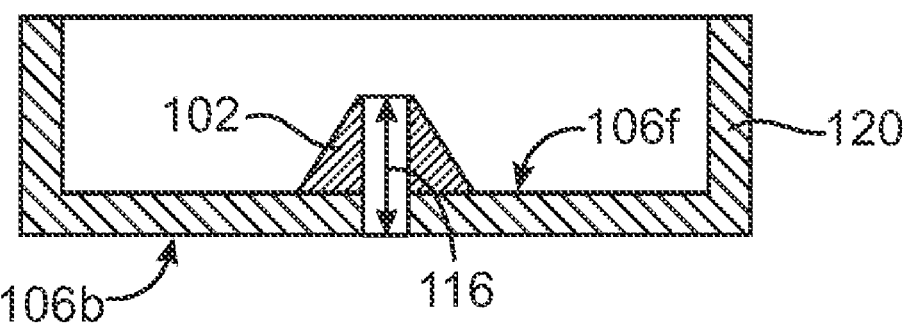

Cut away profiles of two forms of the mold are shown in FIGS. 4F and 4G. In FIG. 4F the riser 102 is shown with a beveled region 114. In FIG. 4G the mold is shown with an aperture 116 that passes through the backside 106b to the top of the riser 102.

Figure 5A:
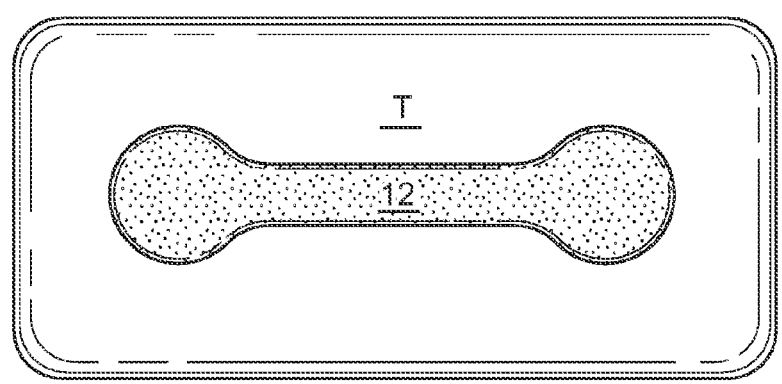
FIGS. 5A-5C show alternative designs of a transducer having a shield.
Figure 5B:
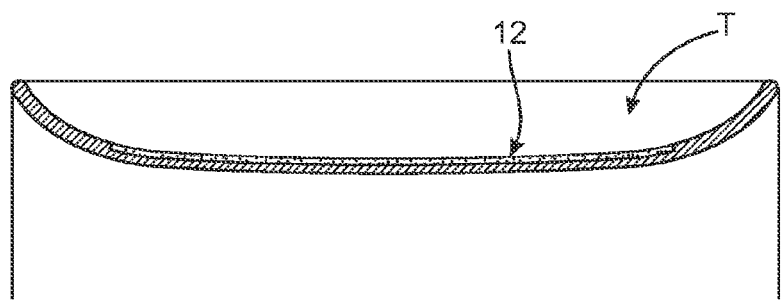

Various alternative forms of a transducer with a shield are now provided. In FIG. 5A a transducer T is shown having a rectangular foot print. The transducer may have a curvature along the length and width of its rectangular form such that when the transducer is used, a long linear "dog bone" shaped region may suffer from the adverse effects of HIFU energy. In this case the shield 12 is shaped to substantially cover the region that would suffer de-lamination from the adverse effects of HIFU operations. A cross section of the rectangular transducer is shown in FIG. 5B.

Figure 5C:
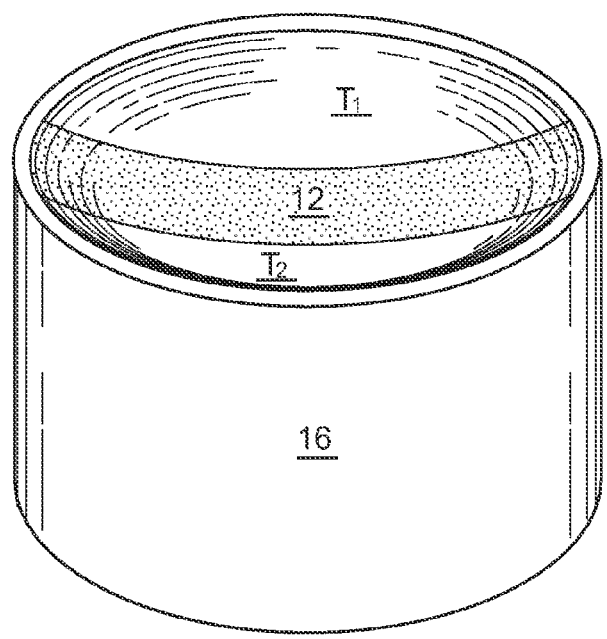

In another embodiment, the transducer is bisected into two transmission regions $T_1$, $T_2$ by a single shield forming a stripe through the transducer face (FIG. 5C). Multiple regions and shields are possible and variations merely depend on planning and forming the shields as desired.

Examples of manufacturing a transducer with a shield are now provided. In a first non-limiting example, an existing transducer can be used and modified to have a shield.

EXAMPLE I

Electrical Isolation

Figure 6A:
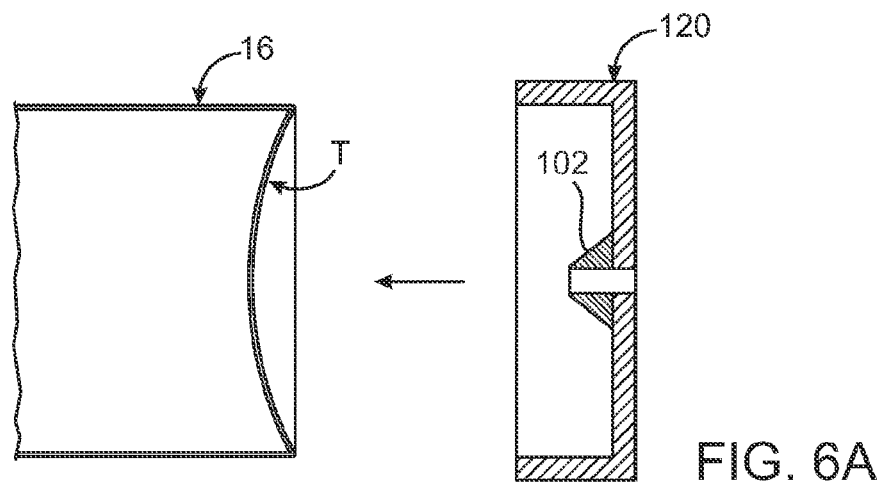
FIGS. 6A-6H illustrates methods of making a transducer with a shield.
Figure 6B:
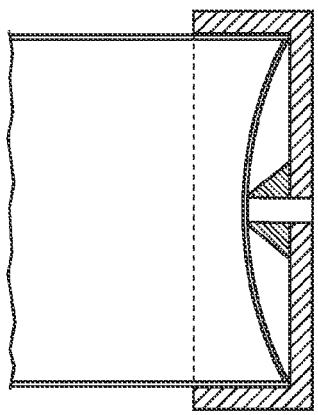
Figure 6C:
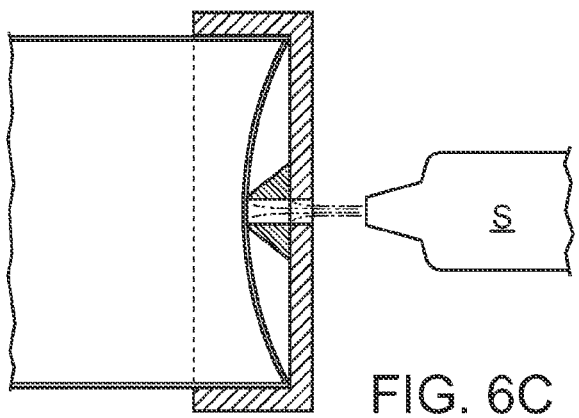
Figure 6C:
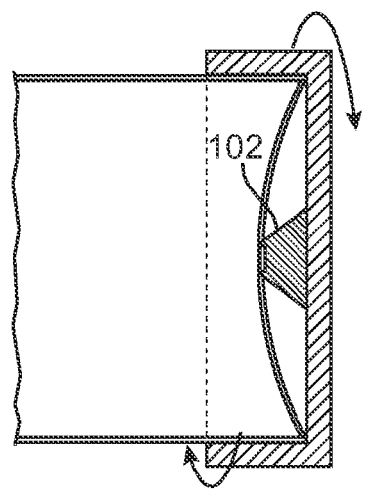

The process of converting an existing HIFU transducer is shown starting in FIG. 6A. Here the transducer T is shown mounted in a housing. A mold with an aperture 120 is fitted over the face of the transducer T and housing 16. Desirably the riser 102 touches the transducer front face when the guide ring is properly fit around the transducer housing. The mold with aperture 120 is desirably secured to the transducer housing so the mold will not move or become unstable during the process steps which follow. Once the mold with aperture 120 is properly placed over the transducer, the surface of the transducer may be roughened to promote physical adhesion of the shield later on. Various mechanisms may be used to roughen the transducer surface. Methods using lasers, chemicals, mechanical etching (such as sand blasting shown in FIG. 6C), or grinding (FIG. 6C') may be used.

The back of the transducer may be treated in a similar fashion allowing for the removal of the metallization layer in a surface area corresponding to the area where the front surface has been roughened. Desirably the back face of the transducer has the metallization layer either scribed to match the roughened surface on the front, or has the metallization removed in an area substantially matching the roughened area on the front, so that when the back is electrically charged, the corresponding area on the back face of the transducer will not form a circuit with the front surface. In this manner there is created a piezoelectric non-driven region of the transducer. This back side can be created using a mold similar to the manner described for making the roughened area on the front surface. Alternatively a core press, grinder, laser, chemical etching means or various other methods of isolating the region are viable embodiments.

Figure 6D:
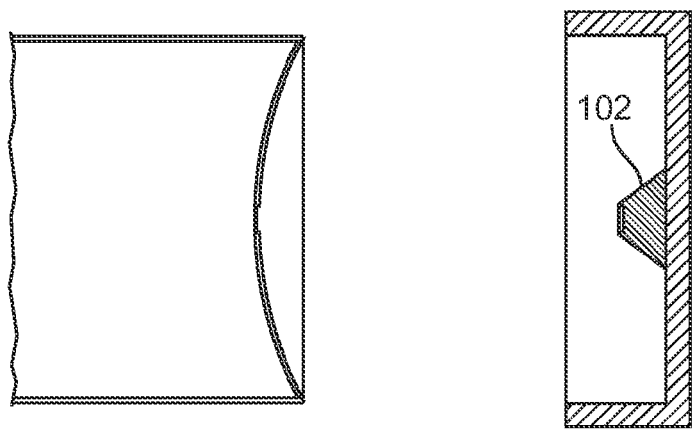
Figure 6E:
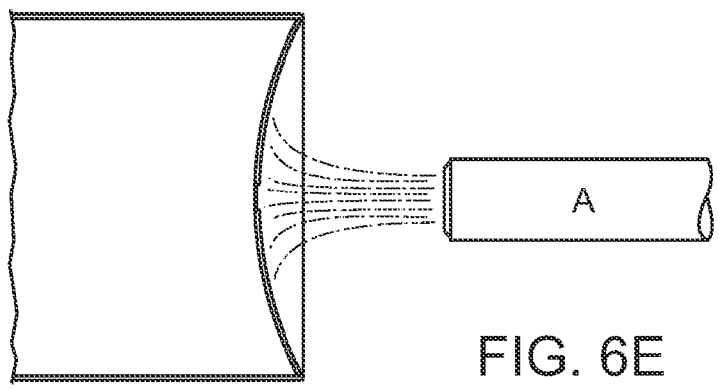
Figure 6F:
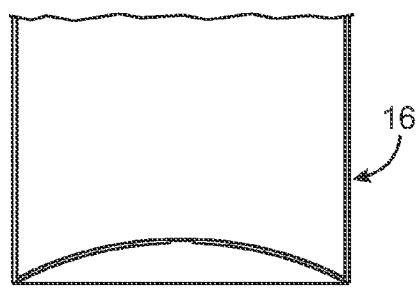
Figure 6G:
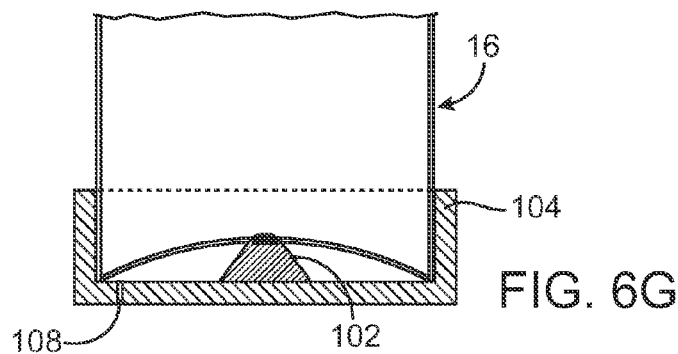
Figure 6H:
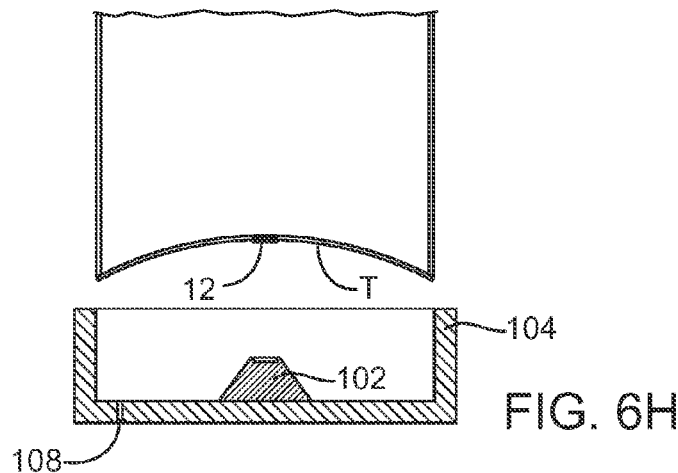

Once the front end has been roughened, the mold is removed from the transducer face and the transducer is cleaned of any remaining debris (FIGS. 6D-6E). A mold having a solid riser 102 with a small recess 114 in the riser is now used to place the shield into place on the transducer face (FIGS. 6F-6H). A measured volume of a polymer P is placed into the recess 114 while the mold 120 is front side 106f facing up. The transducer T is then set on to the mold 120 so the polymer comes into physical contact with the transducer face, and the polymer can bond and set against the transducer. Desirable the polymer does not bond with the mold 120, and if needed the recess may be treated with a non-stick agent to prevent the polymer from bonding with the mold. The mold 120 and transducer T are isolated for sufficient time to permit the polymer to bind to the transducer face and form the shield 12. Once the polymer has set into place, the mold is removed.

It should be understood that the size and depth of the shield may be easily controlled by varying the size of the recess, and the volume of polymer placed into the recess prior to the bonding process. Desirably the recess has a predetermined volume designed to provide the desired level of protection against mechanical damage that the shield is required to provide. Simply stated, a larger shield requires a larger volume of polymer, and thus a larger volume recess in the mold is needed.

EXAMPLE II

Aperture with Filler

In another example, the transducer with a shield may be formed by removing the region of the transducer which is designated to be non-driven. This can be accomplished in a variety of ways. In one embodiment of creating the non-driven region by removal, the material within the volume of the transducer designated to be non-driven can be physically removed. The transducer may be supported in any appropriate fashion and the appropriate volume removed by drilling it out, cutting it out, or otherwise destroying that designated volume of piezoelectric material Once the appropriate volume has been removed, the edges of the aperture are desirably smoothed to provide an even edge for uniform ultrasound generation of the remainder of the transducer. The aperture may now be lined with a non conductive material to preserve the integrity of the circuit, and provide enhanced structural integrity around the rim of the aperture. In addition, the aperture may now be filled with additional material. The aperture liner and filler material may be the same material, or the filler material may be a material having the desirable attributes of absorption/deflection of mechanical energy, or ablative properties. The filler material may be made to the same curvature of the transducer, or it may be shaped to improve deflection or absorption of mechanical energy.

The filler material which serves as a shield may also be axially positioned behind the transducer face, and have additional dimensions to protect the aperture liner if needed.

EXAMPLE III

Non-Driven Ceramic

In yet another embodiment, the non-driven region may be created by purposely rendering the ceramic in the non-driven region unresponsive to electrical impulses by cutting the metallization layer prior to the poling step. This would cause an insulating gap in the metallization layer rendering the isolated portion electrically inactive. The desired polarizing effect within the isolated piezoelectric material would not be produced.

While the invention has been described in numerous embodiments, various modifications will be apparent to those skilled in the art upon study of the present disclosure that will no departing from the spirit or scope of the present invention as defined by the appended claims.

What is claimed is:
1. An apparatus comprising:
   a transducer including a substantially bowl shaped front side, an actively driven region, and a solid non-driven region, the actively driven region surrounding the non-driven region,
   an electrode connected to the front side of the transducer, the electrode including an electrically-isolated portion adjacent to the non-driven region of the transducer; and
   an insulating donut within the non-driven region,
   wherein the transducer is a continuous piece of transducer material.

2. The apparatus of claim 1, wherein the actively driven region includes an aperture, and the non-driven region comprises an insert positioned within the aperture.

3. The apparatus of claim 2, wherein the insert is made of a non-piezoelectric material.

4. The apparatus of claim 2, wherein the insert further comprises a ring of a non-piezoelectric material, and a core.

5. The apparatus of claim 4, wherein the core is made of a polymer.

6. The apparatus of claim 2 wherein the insert completely fills the aperture within the actively driven region.

7. An apparatus comprising:
a transducer including a substantially bowl shaped front side, an actively driven region, and a solid non-driven region, the actively driven region surrounding the non-driven region,
wherein the non-driven region comprises unpoled piezoelectric material and the actively driven region comprises poled piezoelectric material.

8. The apparatus of claim 1, further comprising:
a front metallization layer on the front side of the transducer,
wherein a section of the front metallization layer is absent from the front side to at least in part define the non-driven region.

9. The apparatus of claim 8, wherein the transducer includes a rear side, and further comprising:
a rear metallization layer on the rear side of the transducer,
wherein a section of the rear metallization layer is absent from the rear side to at least in part define the non-driven region.

10. An apparatus comprising:
a transducer including a substantially bowl shaped front side, an actively driven region, and a solid non-driven region, the actively driven region surrounding the non-driven region; and
a front metallization layer on the front side of the transducer, the front metallization layer including a first section on the actively driven region and a second section on the non-driven region, the second section of the front metallization layer separated by a first gap from the first section of the front metallization layer such that the second section of the front metallization layer is electrically isolated from the first section of the front metallization layer.

11. The apparatus of claim 10, wherein the transducer includes a rear side, and further comprising:
a rear metallization layer on the rear side of the transducer, the rear metallization layer including a first section on the actively driven region and a second section on the non-driven region, the second section of the rear metallization layer separated by a second gap from the first section of the rear metallization layer such that the second section of the rear metallization layer is electrically isolated from the first section of the rear metallization layer.

12. The apparatus of claim 7, wherein the transducer is a continuous piece of transducer material, and further comprising:
an electrode connected to the front side of the transducer.

13. The apparatus of claim 12, wherein the electrode includes an electrically-isolated portion adjacent to the non-driven region of the transducer.

14. The apparatus of claim 13, further comprising:
an insulating donut within the non-driven region.

15. The apparatus of claim 13, wherein the electrode includes gaps to form the electrically-isolated portion.

16. The apparatus of claim 15, wherein the gaps are circular.

17. The apparatus of claim 1, further comprising:
a front metallization layer on the front side of the transducer,
wherein a section of the front metallization layer is absent from the front side to at least in part define the non-driven region.

18. The apparatus of claim 17, wherein the transducer includes a rear side, and further comprising:
a rear metallization layer on the rear side of the transducer,
wherein a section of the rear metallization layer is absent from the rear side to at least in part define the non-driven region.

19. The apparatus of claim 10, wherein the first gap is circular.

20. The apparatus of claim 10, wherein the non-driven region comprises unpoled piezoelectric material and the driven region comprises poled piezoelectric material.

21. The apparatus of claim 10, wherein the transducer includes a rear side, and further comprising:
a rear metallization layer on the rear side of the transducer,
wherein a section of the rear metallization layer is absent from the rear side to at least in part define the non-driven region.

* * * * *

UNITED STATES PATENT AND TRADEMARK OFFICE
CERTIFICATE OF CORRECTION

| | | |
|---|---|---|
| PATENT NO. | : 8,334,637 B2 | Page 1 of 1 |
| APPLICATION NO. | : 12/636538 | |
| DATED | : December 18, 2012 | |
| INVENTOR(S) | : Jeffrey R. Crunkilton | |

It is certified that error appears in the above-identified patent and that said Letters Patent is hereby corrected as shown below:

In the Specification:

At column 2, line number 55, change "illustrates" to --illustrate-- and at line number 61, change "illustrates" to --illustrate--.

At column 3, line number 17, change "non piezoelectric" to --non-piezoelectric-- and at line number 55, change "non piezoelectric" to --non-piezoelectric-- and at line number 66, change "are" to --is--.

At column 4, line number 30, after "micro-streaming", delete ",".

At column 5, line number 48, after "(FIG. 1B)", insert --.--.

At column 6, line number 65, change "In" to --If--.

At column 7, line number 13, change "effecting" to --affecting-- and at line number 16, change "non oxidizing" to --non-oxidizing-- and at line number 56, change "are" to --is--.

At column 10, line number 23, change "non conductive" to --non-conductive-- and at line number 53, change "no departing" to --not depart--.

Signed and Sealed this
Twelfth Day of March, 2013

Teresa Stanek Rea
*Acting Director of the United States Patent and Trademark Office*